United States Patent [19]

Abe et al.

[11] 4,362,765

[45] Dec. 7, 1982

[54] METHOD OF MANUFACTURING A GAS SENSING DEVICE

[75] Inventors: Atsushi Abe, Ikoma; Hisahito Ogawa, Katano; Masahiro Nishikawa, Amagasaki; Satoshi Sekido, Yahata; Shigeru Hayakawa, Hirakata, all of Japan

[73] Assignee: Matsushita Electric Industrial Co., Ltd., Osaka, Japan

[21] Appl. No.: 275,254

[22] Filed: Jun. 19, 1981

Related U.S. Application Data

[62] Division of Ser. No. 66,332, Aug. 14, 1979, Pat. No. 4,313,338.

[30] Foreign Application Priority Data

Aug. 18, 1978 [JP] Japan .................. 53-101100
Aug. 18, 1978 [JP] Japan .................. 53-101101
Aug. 23, 1978 [JP] Japan .................. 53-103026

[51] Int. Cl.$^3$ ................................. G01N 27/12
[52] U.S. Cl. ............................ 427/38; 156/610; 156/614; 427/87; 427/101; 427/102; 427/103; 427/99; 427/124; 427/125; 427/126.3
[58] Field of Search ............. 156/610, 614; 427/38, 427/87, 101-103, 99, 124, 125, 126.3; 73/23

[56] References Cited

U.S. PATENT DOCUMENTS

| | | | |
|---|---|---|---|
| 1,888,984 | 11/1932 | Gruss et al. .................. | 73/27 R |
| 3,719,797 | 3/1973 | Andrews, Jr. et al. ........ | 357/28 |
| 3,793,605 | 2/1974 | Fehlner ......................... | 73/23 |
| 4,058,368 | 11/1977 | Svensson et al. ............. | 357/25 |
| 4,091,138 | 5/1978 | Takagi et al. ................. | 427/99 |
| 4,225,634 | 9/1980 | Tanaka et al. ................ | 427/101 |

FOREIGN PATENT DOCUMENTS

2540161 3/1976 Fed. Rep. of Germany .

OTHER PUBLICATIONS

L. Stiblert et al., "Hydrogen Leak Detector Using a Pd-Gate MOS Transistor", *Rev. Sci. Instrum.*, vol. 46, No. 9, pp. 1206-1208, Sep. 1975.

S. Yatsuya et al., "Formation of Ultrafine Metal Particles by Gas-Evaporation Tech.", *Journal of Crystal Growth*, vols. 24-25, pp. 319-322, 1974.

C. G. Granqvist et al., "Ultrafine Metal Particles", *Journal of Applied Physics*, vol. 47, No. 5, pp. 2200-2219, May 1976.

M. Kato, "Preparation of Ultrafine Particles of Refractory Oxides by Gas-Evap. Method", *Japanese Journal of Applied Physics*, vol. 15, No. 5, pp. 757-760, May 1976.

C. Kaito et al., "Electron Microscopic Study of Metal Oxide Smoke Particles Prepared by Burning Metals In Ar-$O_2$ Gas", *Japanese Journal of Applied Physics*, vol. 16, pp. 697-704, May 1977.

S. Ogawa et al., "Tin Fine Particle Film Humidity Sensor", *Report of Government Industrial Research Institute, Osaka*, No. 66, pp. 6-8, 1975.

S. Ogawa et al., "Humidity Sensor Using Fine Particle Film of Tin Oxide", Journal of the Institute of Electronics and Comm. Eng. of Japan, vol. 78, No. 42, pp. 35-38, May 1978.

*Figaro Gas Sensor TGS*, Figaro Engineering Inc., No. 813, Jul. 1978.

*Primary Examiner*—John D. Smith
*Attorney, Agent, or Firm*—Stevens, Davis, Miller & Mosher

[57] ABSTRACT

A gas sensing device comprises a gas sensing element comprising a gas-sensitive resistive film formed of an aggregate of ultrafine particles of a suitable material deposited on the surface of a substrate of an electrical insulator formed with electrodes. In a method of manufacturing such a gas sensing device, a gas-sensitive material is evaporated in a gas atmosphere to provide the gas-sensitive resistive film of ultrafine particles of the material.

9 Claims, 20 Drawing Figures

FIG. IA
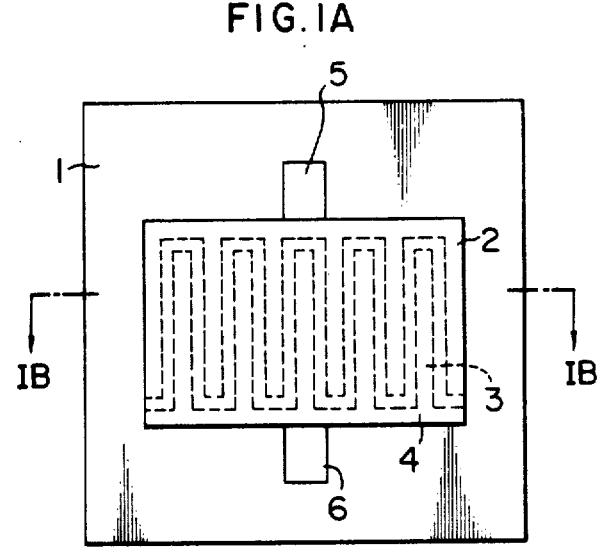
FIG. IB
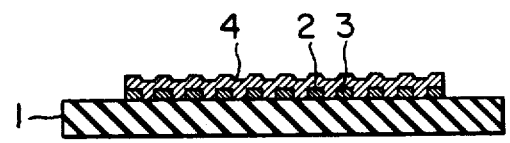
FIG. 2
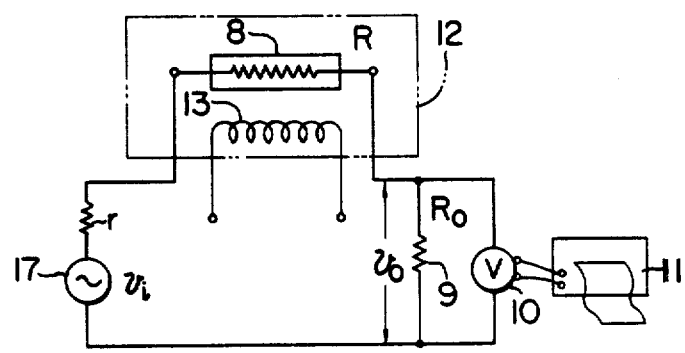

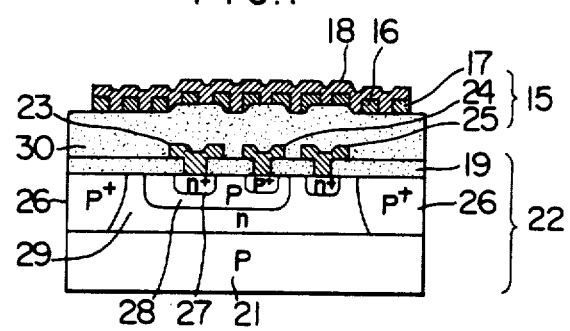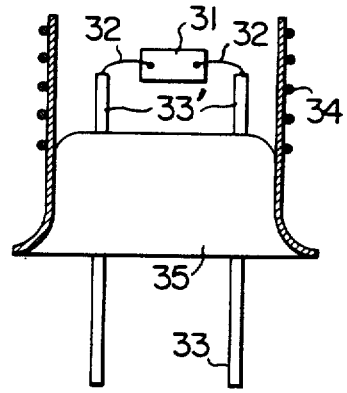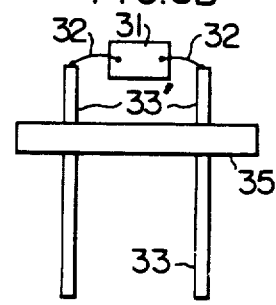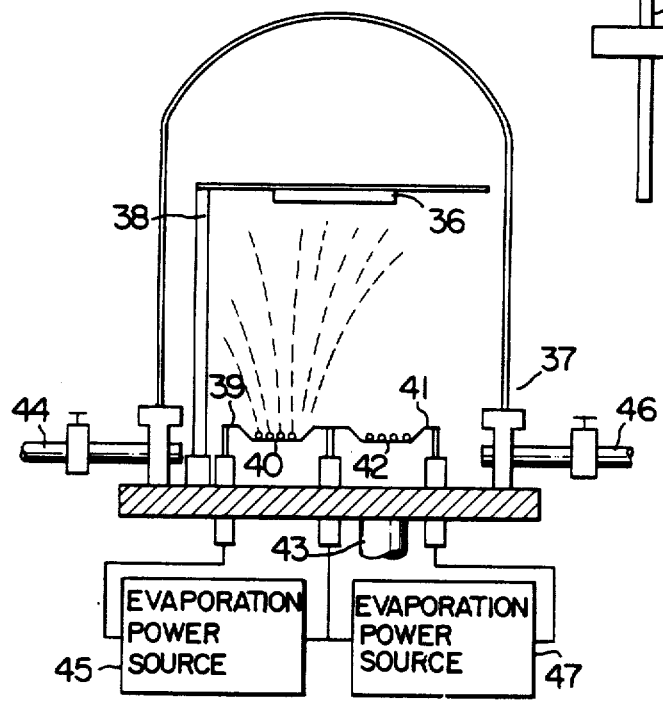

METHOD OF MANUFACTURING A GAS SENSING DEVICE

This is a division of application Ser. No. 66,332 filed Aug. 14, 1979 now U.S. Pat. No. 4,313,338.

This invention relates to gas sensing devices, and more particularly to a novel and improved gas sensing device comprising a gas sensing element comprising a resistive film formed of an aggregate of ultrafine particles of a gas-sensitive material and also to a method of manufacturing such a device.

A small-sized and inexpensive gas sensing device capable of operating with high sensitivity, high selectivity, quick response, low power consumption and high accuracy is now strongly demanded.

Gas sensing elements of the thin-film type, thick-film type and sintered type are well known in conventional gas sensing devices.

A gas sensing element of the sintered type obtained by sintering tin oxide ($SnO_2$) has been put into practical use already. However, this gas sensing element has not had fully satisfactory selectivity since, as is well known, water vapor and gaseous ethyl alcohol provide an obstruction against the successful gas sensing operation of the sensing element when it is used for sensing the presence of a combustible gas, for example, isobutane.

In order that a gas sensing element can sense a gas at an increased speed of response, it is necessary to operate it under heat. In a conventional gas sensing element of the indirectly heated type, a considerable amount of electric power (between several watts and less than 20 watts) had to be supplied to its heating coil, and due to such a high power dissipation it has been difficult to operate the gas sensing element by a dry battery. A conventional gas sensing element of the directly heated type having no heating coil and adapted to heat itself by current supplied thereto also consumed a considerable amount of electric power between several watts and less than 20 watts.

A hydrogen ($H_2$) gas sensing element employing an MOS field effect transistor has also been proposed in which the conventional gate electrode in the form of a thin film of aluminum (Al) is replaced by a thin film of palladium (Pd).

The details of such a gas sensing element are disclosed in, for example, the following two publications:

(1) German Patent Application Laid-open No. 25 40 161 laid open on Mar. 25, 1976

(2) Review of Scientific Instruments Vol. 46, No. 9 (September, 1975), pp. 1206–1208

In the first publication, an MOS field effect transistor having a thin film of Pd is formed together with a diffused resistor in a single semiconductor substrate, and electric power is supplied to the diffused resistor to heat the thin film of Pd by the Joule heat generated from the resistor. In the second publication, a heating coil is employed for heating the gas sensing element, and the temperature of the heating coil is sensed by a thermistor. Due to, however, the fact that the temperature of the gas sensing element is measured indirectly, the operating temperature of the element cannot always be controlled with high accuracy.

Therefore, the packages of the conventional gas sensing devices as well as the conventional gas sensing elements have not always satisfied the conditions or requirements of high response, low power dissipation and high accuracy.

A method of forming ultrafine particles of a metal by means of evaporation in a gas atmosphere (which method will be referred to hereinafter as an in-gas evaporation method) is well known in the art and is disclosed in, for example, the following two publications:

(3) Journal of Crystal Growth vol. 24/25 (1974), pp. 319–322

(4) Journal of Applied Physics vol. 47, No. 5 (May, 1976), pp. 2200–2219

A method of forming ultrafine particles of an oxide is also well known in the art and is disclosed in, for example, the following two publications:

(5) Japanese Journal of Applied Physics Vol 15, No. 5 (May, 1976), pp. 757–760

(6) Japanese Journal of Applied Physics Vol 16, No. 5 (May, 1977), pp. 697–704

However, these publications describe merely a method of forming powders or ultrafine particles of a metal or an oxide and do not describe anywhere a method of providing a resistive film of ultrafine particles of a metal or an oxide.

The fact that a resistive film of ultrafine particles of tin (Sn) formed in a helium (He) gas atmosphere exhibits sensitivity to water vapor is well known and disclosed in, for example, the following two publications:

(7) Report of Government Industrial Research Institute Osaka No. 66 (1975), pp. 6–8

(8) Journal of the Institute of Electronics and Communication Engineers of Japan Vol. 78, No. 42, ED 78-14 (May 29, 1978), pp. 35–38

The latter publication describes that the results of an X-ray diffraction analysis on the composition of such a resistive film of ultrafine particles of Sn prove that a diffraction peak of Sn only appears on the X-ray diffraction curve, and no diffraction peaks of SnO and $SnO_2$ appear on the curve.

All of the aforementioned publications do not describe anywhere that a resistive film of ultrafine particles can be used as a gas-sensitive resistive film. Also, all those publications do not describe anywhere the fact that the gas sensitivity of the film varies greatly depending on the factors including the manufacturing condition, heat treatment condition and operating temperature of the resistive film of ultrafine particles, and also the fact that resistive films of ultrafine particles of different materials differ greatly from one another in their gas sensitivity and gas selectivity.

Many efforts have so far been made by various parties to realize a small-sized and inexpensive gas sensing device having the aforementioned desired operating characteristics such as the high sensitivity, high selectivity, low power dissipation and high accuracy. In spite of these efforts, however, a gas sensing device capable of fully satisfying the above requirements has not yet been produced.

It is therefore a primary object of the present invention to provide a novel and improved gas sensing device comprising a gas sensing element comprising a resistive film formed of an aggregate of ultrafine particles of a gassensitive material or a combination of such materials.

The gas sensing device according to the present invention is especially suitable for use as a gas concentration sensor, a gas alarm, a multifunction gas sensor or the like.

The above object of the present invention is attained by preparing a gas sensing element in which a resistive film formed of an aggregate of ultrafine particles of a gas-sensitive material or a combination of such materials is formed on the surface of a substrate of an electrical insulating material formed with electrodes.

Other objects, features and advantages of the present invention will be apparent from the following detailed description of preferred embodiments thereof taken in conjunction with the accompanying drawings, in which:

FIGS. 1A and 1B are a schematic plan view and a schematic sectional view respectively to show the structure of one form of the gas sensing element comprising the gas-sensitive resistive film formed of an aggregate of ultrafine particles according to the present invention;

FIG. 2 is a circuit diagram of a measuring circuit used for measuring the resistance value of the gas sensing element of the present invention shown in FIGS. 1A and 1B;

FIGS. 6 and 7 are schematic sectional views showing the structure of other embodiments of the gas sensing element according to the present invention;

FIGS. 8A and 8B are schematic elevational views, partly in section, showing the structure of two forms of packages of the gas sensing device according to the present invention;

FIG. 9 is a schematic elevational view, partly in section, showing a method of manufacturing the gas-sensitive resistive film of ultrafine particles according to the present invention;

Figure 3:
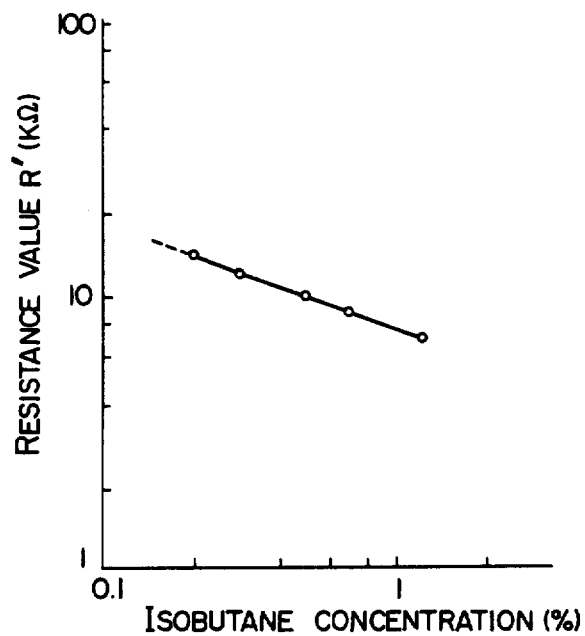
FIGS. 3 to 5 are graphs showing, by way of example, the electrical properties of the gas sensing element of the present invention shown in FIGS. 1A and 1B.

The novel and improved gas sensing device according to the present invention comprises a gas sensing element comprising a resistive film formed of an aggregate of ultrafine particles of a gas-sensitive material or a combination of such materials. The structure of one form of such a gas sensing element will now be described with reference to FIG. 1A which is a schematic plan view and FIG. 1B which is a schematic sectional view taken along the line IB—IB in FIG. 1A.

Referring to FIGS. 1A and 1B, the gas sensing element comprises a substrate 1 of an electrically insulating material such as glass, a ceramic or a synthetic resin. A substrate having a film of an electrical insulating material, such as a substrate of silicon having a surface film of silicon dioxide ($SiO_2$), may also be used as this substrate 1. A pair of electrodes 2 and 3 of comb-shaped pattern are deposited on one of the major surfaces of the substrate 1 in an interdigital form. Each of these comb-shaped electrodes 2 and 3 may be a thin metal film of double layer structure comprising chromium (Cr) and gold (Au) or may be a thin film of a metal oxide such as ruthenium oxide ($RuO_2$), such as can be formed by silk screening an ink or paste containing the metal oxide. A resistive film 4 formed of an aggregate of ultrafine particles of a gas-sensitive material covers the electrodes 2 and 3. The number of teeth of the electrodes 2 and 3 may be increased or the gap therebetween may be narrowed when it is desired to decrease the resistance value of the gas-sensitive resistive film 4 formed of an aggregate of ultrafine particles. The comb-shaped electrodes 2 and 3 are connected to electrode terminals 5 and 6 respectively to be connected to an external circuit.

The comb-shaped electrode pattern is illustrated in FIGS. 1A and 1B by way of example, and it is apparent to those skilled in the art that the electrodes 2 and 3 may have any other suitable shape.

The gas-sensitive resistive film 4 formed of an aggregate of ultrafine particles may be a single-layer film formed of ultrafine particles of a metal oxide, for example, an oxide of Sn, Mn, Cu, Mo, Ni, Zn, Ti, In, Cd, Fe, Ag, Bi, Pb, Ca, Mg, V, Nb or W. The film 4 may be a single-layer formed of ultrafine particles of a mixture of metal oxides of different kinds, or may be a film formed of a mixture of ultrafine particles of metal of, for example, Sn and ultrafine particles of an oxide of, for example, Mn, or may be a multi-layer film including a combination of a single-layer film formed of ultrafine particles of a metal oxide for example, an oxide of Sn, and a single-layer film formed of ultrafine particles of a metal, for example, Pd. The film 4 may be a multi-layer film including a combination of single-layer films formed of ultrafine particles of a metal oxide such as an oxide of Sn. In this case, a single-layer film formed of ultrafine particles of the oxide of Sn having a smaller means particle diameter may be superposed on a single-layer film formed of ultrafine particles of the same oxide but having a larger mean particle diameter. The film 4 may also be a multi-layer film comprising a selected combination of various films as described above. The ultrafine particles of any one of the metals above described are oxidized at their surface when exposed to air subsequent to the formation. Thus, in the present description, ultrafine particles of a metal are defined as those which, when subjected to an X-ray diffraction analysis after the formation and the exposure to air but before a heat treatment, exhibit a peak peculiar to the metal on the X-ray diffraction curve.

Although FIGS. 1A and 1B show a single gas-sensitive resistive film 4 of ultrafine particles formed on the electrically insulating substrate 1, those skilled in the art will readily understand that a plurality of such films of the same material may be formed on the single substrate and that a plurality of such films of different materials may be formed on the single substrate.

The gas sensing element comprising the gas-sensitive resistive film formed of an aggregate of ultrafine particles employed in the gas sensing device according to the present invention differs entirely in characteristics from the gas sensing elements of the thin-film type, thick-film type and sintered type employed in the prior art gas sensing devices.

Thus, the proposal of the present invention, in which such a gas-sensitive resistive film formed of an aggregate of ultrafine particles is formed to cover a pair of electrodes on an electrical insulating substrate, and the resistance value of the resistive film formed of an aggregate of ultrafine particles variable depending on the concentration of gases in a gas atmosphere is measured for the quantitative measurement of the concentration of gases such as isobutane gase and water vapor, is quite novel in that it has not been made hitherto.

The gas-sensitive resistive film formed of an aggregate of ultrafine particles is formed by the so-called in-gas evaporation method which is a sort of a process of vapor growth in which a evaporating material is heated to evaporate in a gas atmosphere at a pressure of, for example, about 0.1 Torr to about 100 Torr, and the atoms of the evaporated material collide with the gas in the gas atmosphere to produce ultrafine particles of the material. The film thus obtained is an aggregate of ultrafine particles each of which is a single crystal. Therefore, the gas sensing element according to the present inventoin has an extraordinarily large surface area for contact with gases such as isobutane gas and water vapor whose concentrations are to be measured, when compared with that of the prior art gas sensing element of the thin-film type.

The ultrafine particles produced by the so-called in-gas evaporation method have a mean particle diameter between more than 10 Å and several hundred Å, and thus, the mean particle diameter is extraordinarily small compared with that of the powdery material used for forming the prior art gas sensing element of the thick-film type or of the sintered type. Therefore, the gas sensing element according to the present inventoin has an extraordinarily large surface area for contact with measured gases, when compared also with that of the prior art gas sensing element of the thick-film type or of the sintered type.

In the production of the gas-sensitive resistive film formed of an aggregate of ultrafine particles by the so-called in-gas evaporation method, heat treatment is unnecessary for the formation process of the film. In contrast, in the production of the prior art gas sensing element of the thick-film type or of the sintered type, a powdery material used for the production of the gas sensing element is sintered at a very high temperature as is commonly known, resulting in a remarkable increase in the mean particle diameter of the particles relative to the mean particle diameter of, for example, several $\mu$ of the starting powdery material.

It will be apparent from the above discussion that the surface energy and surface acitivity of the gas sensing element comprising the gas-sensitive resistive film formed of an aggregate of ultrafine particles according to the present invention are extraordinarily high compared with those of the prior art gas sensing elements of the thin-film type, the thick-film type and the sintered type. For the above reason, the gas sensing element according to the present invention can sense the concentration of gases such as isobutane gas and water vapor with very high sensitivity.

The resistance value of the gas-sensitive resistive film formed of an aggregate of ultrafine particles according to the present invention can be measured by a method similar to that commonly employed for the prior art gas sensing device. According to this method, the gas sensing element comprising the gas-sensitive resistive film of ultrafine particles is connected in series with a reference resistor, and a predetermined voltage is applied across the series connection so as to measure the resistance value of the gas sensing element by measuring the divided voltage.

FIG. 2 shows a circuit for measuring the resistance value of the gas sensing element comprising the gas-sensitive resistive film of ultrafine particles according to the present invention. Referring to FIG. 2, an oscillator 17 acting as a power source of an AC voltage Vi and having an internal resistance value r is connected to the gas sensing element 8 comprising the gas-sensitive resistive film formed of an aggregate of ultrafine particles, the resistance value R of which is to be measured. This gas sensing element 8 is provided with means to be heated by a heater 13 disposed adjacent thereto. This heater 13 may be in contact or may not be in contact with a gas atmosphere whose concentration is to be measured. A reference resistor 9 having a resistance value Ro is connected in series with the gas sensing element 8. An AC volt meter 10 is connected in parallel with the reference resistor 9, and a recorder 11 is provided to record the measured voltage. The AC voltage measured by the volt meter 10 is converted into the corresponding DC voltage which is applied to the recorder 11.

The region 12 enclosed by the broken lines in FIG. 2 defines the gas atmosphere whose concentration is to be measured, and the gas sensing element 8 provided with the means to be heated by the heater 13 is disposed within this gas atmosphere. The resistance value R of the gas sensing element 8, variable in relation to variations in the concentration of the gas atmosphere, is read as a corresponding variation in the division ratio of the voltage $V_i$. That is, the voltage $V_o$ across the reference resistor 9 is given by $$V_o = \frac{R_o}{r + R + R_o} \cdot V_i$$

Therefore, the resistance value R of the gas sensing element 8 is expressed as $$R = (V_i/V_o - 1)R_o - r$$

Since the internal resistance value r of the oscillator 17 is sufficiently small compared with the resistance value R of the gas sensing element 8, this resistance value R may be approximated as $$R = (V_i/V_o - 1)R_o$$

It is needless to say that the internal resistance value of the AC volt meter 10 is sufficiently large compared with the resistance value $R_o$ of the reference resistor 9.

Various methods have been used hitherto as a means for heating the gas sensing elements in the prior art gas sensing devices. These methods include a method in which current is supplied to a heating coil so as to indirectly heat the gas sensing element by the heat generated from the heating coil, a method in which current is supplied to the gas sensing element itself so as to cause self-heating thereby directly heating the gas sensing element, and a method in which current is supplied to a diffused resistor formed together with the gas sensing element in a portion of a semiconductor integrated circuit chip so as to generate the Joule heat in the diffused resistor thereby indirectly heating the gas sensing element. In the case of the gas sensing element of the gas sensing device according to the present invention too, a heating means similar to that described above can be employed. It has been ascertained that, besides the heating means described above, another heating means can be effectively used in which power is supplied to a pn-junction element such as a transistor or a diode so as to generate heat in the pn-junction element thereby indirectly heating the gas sensing element according to the present invention. Utilization of such a pn-junction element as a heat generating element provides such a great merit that a large current can be supplied at an applied voltage of low level lower than about 1 volt. However, due to the fact that the operation of the pn-junction element tends to become unstable when the temperature of the heated pn-junction element exceeds 180° C. to 200° C., there is a limit in the temperature at which the pn-junction element can operate stably as the heat generating element.

It is needless to say that this heat generating element is preferably disposed in a portion of the electrically insulating substrate or of a supporting member supporting the electrically insulating substrate at a position as close to the gas-sensitive resistive film of ultrafine particles as possible.

It is apparent that not only a thick-film resistor, a thin-film resistor or a diffused resistor, but also, a resistor formed by ion implantation, a resistor in the form of polycrystalline silicon or like resistor can be used as the resistive element acting as the heat generating element.

In the case of any one of the prior art gas sensing devices, the method of measuring the temperature of its gas sensing element has comprised measuring the temperature of the heating coil by means of the thermister, thereby indirectly measuring the temperature of the gas sensing element. In the case of the gas sensing device according to the present invention, a resistive element or a pn-junction element is formed as an integral part of the electrically insulating substrate formed with the gas-sensitive resistive film formed of an aggregate of ultrafine particles or as an integral part of a supporting member supporting the electrically insulating substrate, and such an element is disposed at a position as close to the gas-sensitive resistive film of ultrafine particles, as described hereinbefore, so that the resistive element or the pn-junction element can be used for the direct measurement of the temperature of the gas sensing element.

The resistive element used for the direct measurement of the temperature of the gas sensing element may be a thick-film resistor, a thin-film resistor, an ion implanted resistor, a polycrystalline silicon resistor or the like. Also, the pn-junction element may be a transistor, a diode or the like.

It is well known that the resistance value of the resistive element above described is dependent upon the temperature. It is also well known that the pn-junction element above described shows similar temperature dependence. That is, when, for example, the base and the collector of a transistor are electrically connected, a small current of the order of, for example, 10 $\mu$A is supplied to flow between the emitter and the base of the transistor, and the base-emitter voltage $V_{BE}$ is measured in such a condition, the value of this base-emitter voltage $V_{BE}$ decreases at a rate of about 2 mV/°C. in relation to the increase in the temperature. Thus, when this voltage $V_{BE}$ whose value decreases in a 1:1 relation with the temperature increase is fed back to the control circuit controlling the electric power supplied to the heater, the temperature of the gas sensing element, hence, that of the gas-sensitive resistive film of ultrafine particles can be maintained constant with high accuracy.

In the case of the prior art gas sensing device, its gas sensing element has been disposed in a location remote from the thermistor. In the case of the gas sensing device according to the present invention, the gas sensing element comprising the gas-sensitive resistive film formed of an aggregate of ultrafine particles and the associated temperature sensing element for sensing the temperature of the gas sensing element are formed as the integral parts of the electrically insulating substrate or of the supporting member supporting the substrate and are very closely spaced apart from each other. Therefore, the temperature sensing element can make a quick response to variations in the temperature of the gas atmosphere whose concentration is to be measured, so that the temperature of the gas-sensitive resistive film of ultrafine particles can be more accurately controlled than hitherto.

It is apparent that the gas sensing element in the gas sensing device according to the present invention may not require the temperature sensing element provided for sensing the temperature of the gas sensing element when the temperature of the gas atmosphere whose concentration is to be measured does not vary appreciably, and also, the power voltage for actuating the gas sensing device does not fluctuate appreciably. In such a case, however, it is desirable to accurately control the electric power supplied to the heater.

When, for example, a gas-sensitive resistive film formed of an aggregate of ultrafine particles of tin oxide was heated up to 300° C., and its resistance value R' in an atmosphere of isobutane gas was measured by the circuit shown in FIG. 2, the resistance value R' of the gas-sensitive resistive film of ultrafine particles of tin oxide exhibited a gas concentration dependence as shown in FIG. 3. Therefore, the concentration of isobutane gas can be readily determined on the basis of the measured value of R' by previously preparing the calibration curve shown in FIG. 3. Thus, when, for example, R'=14 k$\Omega$, the concentration of isobutane gas is determined to be 0.2%. It is important to previously set the optimum heating temperature so as to attain effective heating.

Figure 4:
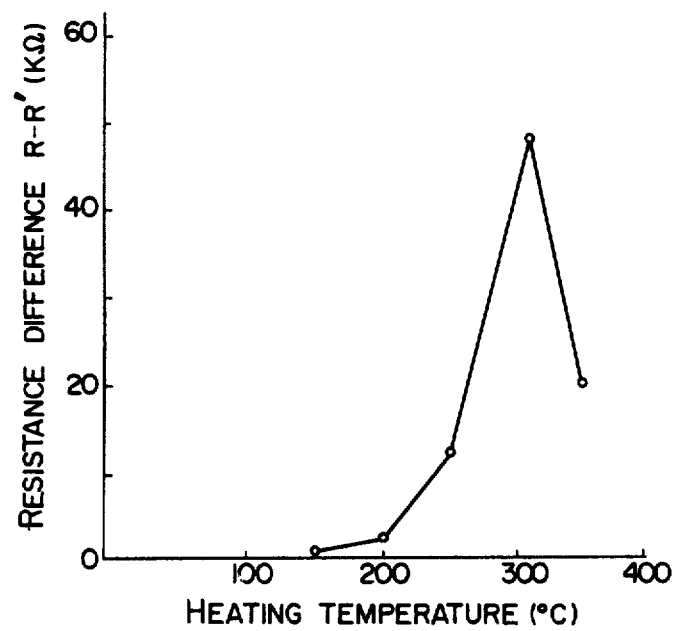

FIG. 4 shows the temperature dependence of the difference (R−R') between the resistance value R of the gas sensing element measured in the absence of isobutane gas and the resistance value R' measured in the presence of isobutane gas. It will be seen from FIG. 4 that the value of the difference (R−R') is largest when the gas sensing element is heated up to 300° C. On the other hand, the ratio (R−R')/R and the ratio R'/R are substantially constant at temperatures above about 300° C. regardless of the heating temperature.

Figure 5:
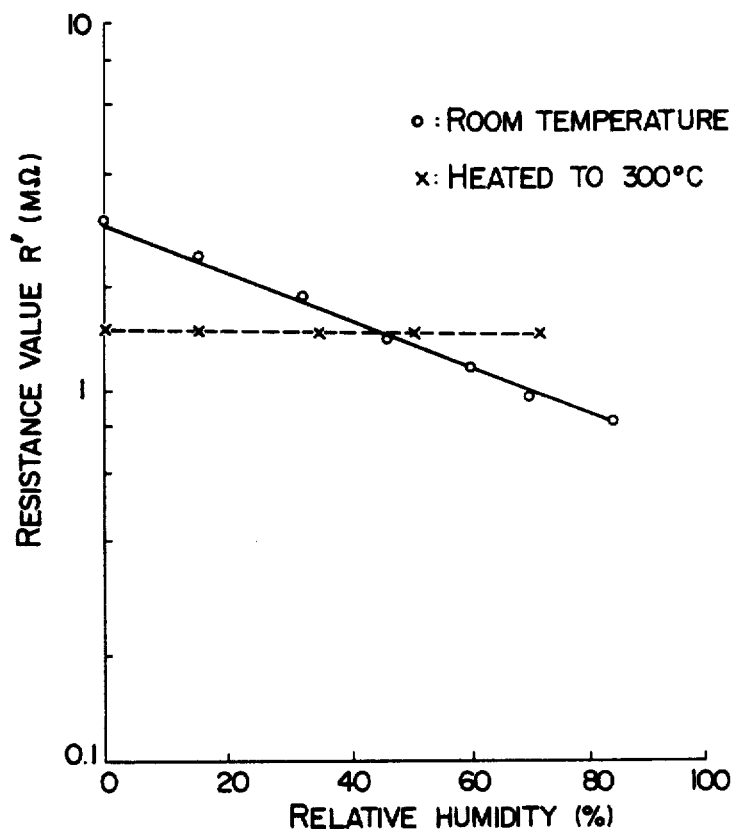

The resistance value R' of the gas sensing element is 7 k$\Omega$ in gaseous ethyl alcohol ($C_2H_5OH$) having a concentration of 0.07%. The solid curve in FIG. 5 represents the relative humidity dependence of R' at the room temperature of 25° C. At 300° C., the value of R' does not change, as shown by the broken curve in FIG. 5. It will thus be seen that the operation of the gas sensing element comprising the gas-sensitive resistive film formed of an aggregate of ultrafine particles according to the present invention is not adversely affected by the presence of water vapor when it is operated at the temperature of 300° C. Therefore, the present invention obviates such a prior art problem that the presence of water vapor obstructs the successful measurement of the concentration of isobutane gas, although the above problem has been practically encounted during the measurement of the isobutane gas concentration by the prior art gas sensing element of the sintered type obtained by sintering powders of $SnO_2$. Thus, when the gas sensing element according to the present invention is operated alternately at the room temperature of 25° C. and at 300° C., the single gas sensing element can sense both the concentration of water vapor and the concentration of isobutane gas. More precisely, the gas sensing element is heated up to 300° C. during the measurement of the concentration of the isobutane gas and is cooled down to the room temperature of 25° C. during the measurement of the relative humidity. The relative humidity may be measured by temporarily heating the gas sensing element for a short time immediately before the measurement of the relative humidity and then cooling the gas sensing element down to the room temperature of 25° C.

Although the mechanism with which the gas-sensitive resistive film of ultrafine particles according to the present invention can very sharply and selectively respond to or sense the concentration of gases such as isobutane gas and water vapor in the manner above described has not yet been fully clarified, this mechanism is the important characteristic feature of the gas-sensitive resistive film of ultrafine particles, according to the present invention.

The shape and structure of the gas sensing element according to the present invention are illustrated in FIG. 1 merely by way of example, and it is apparent that there are various other forms of such a gas sensing element.

Figure 6:
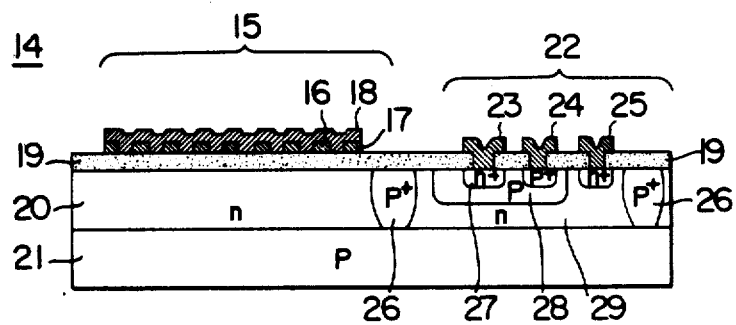

FIG. 6 shows the structure of another embodiment of the gas sensing element according to the present invention and is a schematic sectional view of a semiconductor integrated circuit chip 14. Referring to FIG. 6, the left-hand portion 15 of the chip 14 operates as a gas sensing part which comprises a gas-sensitive resistive film 18 formed of an aggregate of ultrafine particles covering a pair of comb-shaped electrodes 16 and 17 formed on an electrically insulating film 19 which may be a film of $SiO_2$. The right-hand portion 22 of the chip 14 operates as an active part of the semiconductor integrated circuit, and an npn transistor is illustrated as a typical example of the active part. The transistor of such a structure or a suitable resistive element is formed as a part of the chip 14, and a suitable wiring arrangement is provided by evaporation of a conductive metal, so as to operate as a temperature sensing element for sensing the temperature of the gas-sensitive resistive film 18 of ultrafine particles and/or a heat generating element for heating the gas-sensitive resistive film 18.

Referring to FIG. 6, an n-type epitaxial layer 20 is formed on one of the major surfaces of a p-type substrate of silicon 21, and a p+-type diffused region 26 extends through this layer 20 to define an n-type island region 29. A p-type base region 28 and an n+-type emitter region 27 are formed in this island region 29. An emitter electrode 23, a base electrode 24 and a collector electrode 25 are deposited on the regions 27, 28 and 29 respectively.

In the structure shown in FIG. 6, elements such as a transistor and a resistor constituting other parts of the semiconductor integrated circuit are not formed beneath the gas sensing part 15 sensing the concentration of gases such as isobutane gas and water vapor. It is apparent, however, that such elements may be formed beneath the gas sensing part 15.

FIG. 7 shows a modification of the structure shown in FIG. 6. Referring to FIG. 7, the gas sensing part 15 is disposed above the active part 22 of the semiconductor integrated circuit chip. In this modification, an $SiO_2$ film 30 is deposited over the entire surface of the $SiO_2$ film 19 by the Chemical Vapor Deposition ("CVD") method after forming the electrodes 23, 24 and 25, and then, the comb-shaped electrodes 16, 17 and the gas-sensitive resistive film 18 of ultrafine particles shown in FIG. 6 are formed on the $SiO_2$ film 30. In FIGS. 6 and 7, electrode leads are not shown to avoid confusion.

The $SiO_2$ films 19 and 30 shown in FIGS. 6 and 7 are as thick as about $1\mu$ at the most, so that the temperature difference between the gas-sensitive resistive film 18 of ultrafine particles and the temperature sensing element or the heat generating element formed in the semiconductor integrated circuit chip is quite negligible. Therefore, the gas-sensitive resistive film of ultrafine particles can be efficiently heated, and the power dissipated by the heat generating element can be correspondingly reduced. It is apparent that the operating temperature of the gas-sensitive resistive film of ultrafine particles can also be measured with correspondingly high accuracy.

Employment of the structure of the gas sensing element shown in FIGS. 6 or 7 can provide a gas sensing device which comprises an integral combination of a gas sensing part and a semiconductor integrated circuit part operating in response to a variation in the output of the gas sensing part. That is, the gas sensing part comprising the gas-sensitive resistive film of ultrafine particles capable of sensing the concentration of gases such as isobutane gas and water vapor with very high sensitivity can be formed in a single semiconductor chip in an integral relation with at least one of a heat generating part heating the gas sensing part, a temperature sensing part sensing the temperature of the gas sensing part, a control part controlling the heating temperature and a load drive part driving a load such as a buzzer or like alarm or a load such as a display. In another form, only the gas sensing part, the heat generating part heating the gas sensing part and the temperature sensing part sensing the temperature of the gas sensing part are formed in a semiconductor chip, while the control part controlling the heating temperature and the load drive part driving the buzzer or like alarm or the display are formed in another semiconductor chip, and these two semiconductor chips are disposed or supported on a single supporting member to provide an integral assembly. It is apparent that various other forms of such an integral assembly may be provided. For example, the gas-sensitive resistive film formed of an aggregate of ultrafine particles may be directly formed as a part of the supporting member, or a semiconductor chip formed with the gas-sensitive resistive film of ultrafine particles may be mounted on a portion of the supporting member.

The circuit structure of the parts such as the control part controlling the heating temperature and the load drive part driving the buzzer or like alarm or the display is not illustrated in FIGS. 6 and 7, since such a structure is well known in the art.

As one of the means for minimizing the power dissipation required for heating the gas-sensitive resistive film of ultrafine particles, the gas-sensitive resistive film of ultrafine particles may be formed above the area in which heat is generated in a large quantity in the semiconductor integrated circuit chip, for example, above the area which includes the power transistor in the load drive circuit or the like.

The two forms of the gas sensing device of the present invention shown in FIGS. 6 and 7 have the inherent tendency of exhibiting uniform sensing characteristics. Further, due to the fact that the usual technique for the manufacture of semiconductor integrated circuits can be directly applied to the production, such gas sensing devices of very small size can be relatively easily mass-produced.

Another embodiment of the gas sensing device comprising the gas-sensitive resistive film of ultrafine particles will then be described. Two gas-sensitive resistive films formed of an aggregate of ultrafine particles having different resistance values $R_{x1}$ and $R_{x2}$ in air respectively are connected in series, and one of them or that having the resistance value $R_{x2}$ is shielded from a gas atmosphere to operate as a resistive film of ultrafine particles which is non-sensitive to the gas. The reference resistor 9 in FIG. 2 is replaced by this non-gas-sensitive resistive film of ultrafine particles having the resistance value $R_{x2}$, and the two resistive films are heated up to the same temperature. In this embodiment, the two characteristics, described below, of the gas-sensitive resistive film of ultrafine particles are utilized. According to the first characteristic, the ratio $R_{x1}/R_{x2}$ ($=K$) between the resistance values $R_{x1}$ and $R_{x2}$ of two resistive films of ultrafine particles of, for example, tin oxide remains constant independently of the operating temperature, although these two resistive films having respectively the films having the respectively different resistance values $R_{x1}$ and $R_{x2}$ exhibit a complex and great temperature dependence. According to the second characteristic, the ratio $R_{x1G}/R_{x1}$ ($=C$) remains constant independently of the value of $R_{x1}$, where $R_{x1G}$ is the resistance value of the resistive film of ultrafine particles of tin oxide at a certain gas concentration, and $R_{x1}$ is its resistance value in air. It is to be noted, however, that the resistance value $R_{x2}$ remains constant independently of the gas concentration as the film is shielded from the gas. Therefore, the voltage $V_o$ across the resistive film having the resistance value $R_{x2}$ is given by $$V_o = \frac{R_{x2}}{R_{x1G} + R_{x2}} \cdot V_i$$

$$= \frac{1}{\frac{R_{x1G}}{R_{x2}} + 1} \cdot V_i$$

$$= \frac{1}{K \frac{R_{x1G}}{R_{x1}} + 1} \cdot V_1$$

$$= \frac{1}{K \cdot C + 1} \cdot V_1$$

Therefore, in the embodiment of the gas sensing device above described, the same output voltage $V_o$ appears at the same gas concentration in spite of possible fluctuations in the value of $R_{x1}$ during the manufacture. It will thus be understood that the modification or correction of the resistance value of the reference resistor to compensate the fluctuations in the resistance value of the gas sensing element, as has been the case with the prior art gas sensing device, is not necessarily required.

It will be apparent from the above description that the gas sensing device according to the presently described embodiment of the present invention, which is simple in construction and can operate with high accuracy, can be relatively easily manufactured and is thus industrially valuable.

Other embodiments of the gas sensing device comprising the gas-sensitive resistive film formed of an aggregate of ultrafine particles according to the present invention will be described with reference to FIGS. 8A and 8B.

Referring to each of FIGS. 8A and 8B, an electrically insulating substrate 31 formed with a gas-sensitive resistive film of ultrafine particles is supported in space by a pair of wires 32 which provide lead wires for the gas-sensitive resistive film. These wires 32 may be made of platinum containing iridium and are connected at the other end to portions 33' of posts 33 extending through a package 35 which may be made of a metal, a ceramic or a molded resin.

In FIG. 8A, the electrical insulating substrate 31 is heated by a heating coil 34 formed by winding a wire of Kanthal (trade name).

As described hereinbefore in the embodiments of the gas sensing device according to the present invention, a resistive element or a pn-junction element for the temperature sensing purpose is naturally provided in a portion of the electrical insulating substrate 31 so as to measure the temperature of the gas-sensitive resistive film of ultrafine particles formed on the substrate 31. In order to minimize the time constant of heating and cooling the electrical insulating substrate 31 and also to minimize the power dissipation required for heating, it is needless to say that the thermal capacity of the electrically insulating substrate 31 is desirably as small as possible.

The manner of temperature control in the prior art gas sensing device has been such that the electrically insulating substrate 31 is mounted on the package 35, and a thermistor is brought into contact with a portion of the heating coil 34 for indirectly controlling the temperature of the electrically insulating substrate 31. The prior art gas sensing device has been encountered with various problems as pointed out below in its practical use. The present invention can obviate these problems by constructing the gas sensing device in the package form shown in FIG. 8A.

The first problem of the package of the prior art gas sensing device resides in the fact that the thermistor is spaced apart by a considerable distance from the electrically insulating substrate 31 as will be readily understood at a glance on FIG. 8A, and consequently, the temperature of the electrically insulating substrate 31 cannot be accurately measured. The second problem resides in the fact that, due to the possible variations in the shape and the number of turns of the heating coil 34, in the position of the electrically insulating substrate 31 relative to the package 35, in the arrangement of the thermistor holder relative to the heating coil 34 and in the thermal capacity of the package 35, the temperature of the heating coil 34 actually sensed by the thermistor, hence, the temperature of the electrically insulating substrate 31 must be compensated in relation to the electric power supplied to the heating coil 34, and the steps of inspection and adjustment are additionally required resulting in an industrial disadvantage. The third problem resides in the fact that a large quantity of heat is dissipated by the package 35 itself resulting in a higher power dissipated and a larger time constant of heating, since the electrically insulating substrate 31 heated by the heating coil 34 is not supported in space.

The large time constant of heating is especially undesirable in an operating condition in which the electrically insulating substrate 31 is heated during only the measurement of a gas concentration or in an operating condition in which a gas concentration is measured by temporarily heating the electrically insulating substrate 31 up to several hundred °C. and then cooling down to the room temperature of 25° C. or to a temperature lower than the previous heating temperature.

In the gas sensing device of the present invention shown in FIG. 8A, the temperature of the electrically insulating substrate 31 is sensed by the temperature sensing element incorporated in the substrate 31, so that the operating temperature of the gas sensing element can be sensed with a higher accuracy than hitherto. In addition, due to the fact that the electrically insulating substrate 31 is supported in space, the power dissipated is lower than hitherto, and also, the speed of response to heat is quicker than hitherto. Although a pair of lead wires for the temperature sensing element are additionally required, such wires are not illustrated in FIG. 8A.

In the gas sensing device shown in FIG. 8B, the electrically insulating substrate 31 comprises a temperature sensing element and a heat generating element. In this case, two pairs of lead wires for these elements are additionally required although not illustrated in FIG. 8B.

The embodiments of the gas sensing device shown in FIGS. 8A and 8B are advantageous over the prior art in that not only the power dissipated is lowered but also the speed of response to heat is increased. Especially, the structures shown in FIGS. 8A and 8B are advantageous over the prior art in that the heated electrically insulating substrate 31 can be cooled down at a faster rate to the room temperature of 25° C. or to a temperature lower than the previous heating temperature.

Figure 16A:
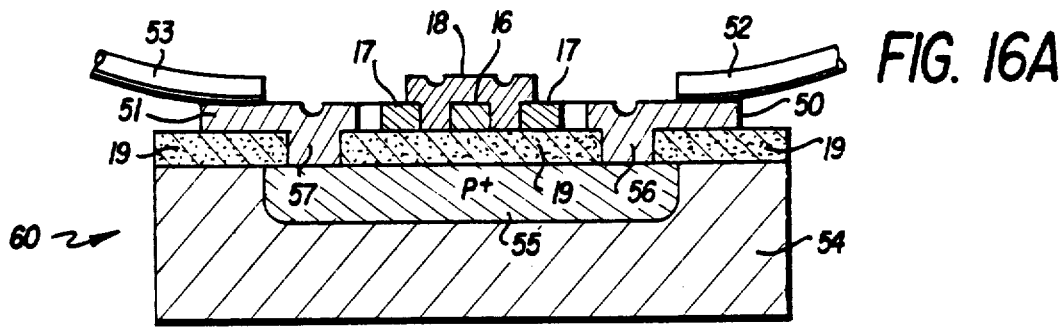
FIG. 16A shows a sectional side view of a pn-junction element which may be used in the present invention.
Figure 16B:
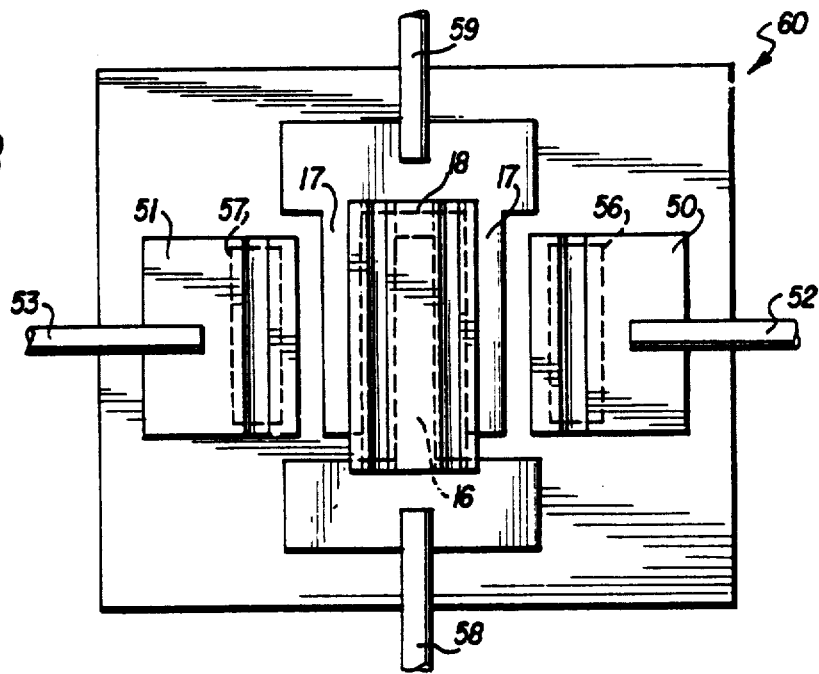
FIG. 16B shows a top view of the element of FIG. 16A.
Figure 16C:
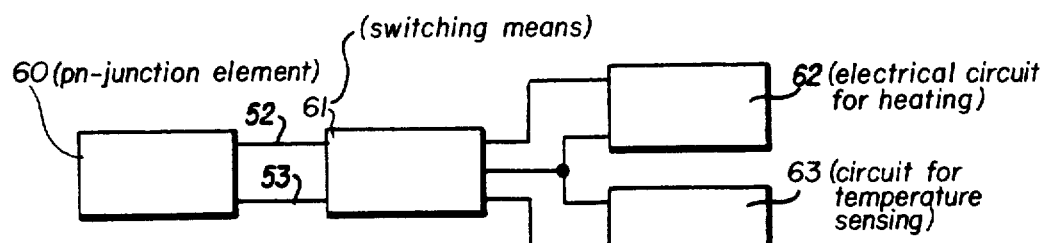
FIG. 16C shows a block diagram of a selection circuit using the element of FIGS. 16A and 16B.

A modification for eliminating one pair of lead wires in the embodiment shown in FIG. 8B will now be described. This is realized by an arrangement in which the heat generating element used for heating the gas-sensitive resistive film of ultrafine particles is adapted to function also as the temperature sensing element used for sensing the temperature of the gas-sensitive resistive film of ultrafine particles. In other words, the single element is arranged to carry out the two functions by automatically or manually changing over the circuit actuating the element to operate as the heat generating element and the circuit actuating the element to operate as the temperature sensing element. FIGS. 16A and 16B show a pn-junction element 60 provided in place of the active part 22 and FIG. 16C is a block diagram of a selection circuit for use in selectively changing over the pn-junction element 60 to operate it as the heat generating element or as the temperature sensing element. In the Figures, 50 and 51 are electrode for a p+ diffusion resistor 55, 52 and 53 wires, 54 an n-type semiconductor substrate, 56 and 57 openings, 58 and 59 wires for the comb-shape electrodes, 61 a switching means for this purpose, 62 an electrical circuit connected for actuating the pn-junction element for the heating purpose and 63 an electrical circuit connected for actuating the pn-junction element for the temperature sensing purpose.

In each of FIGS. 8A and 8B, an explosion-proof cap is not illustrated to avoid confusion.

A method of manufacturing the gas sensing element comprising the gas-sensitive resistive film of ultrafine particles according to the present invention will now be described. By way of example, a method of manufacturing a gas sensing element comprising a multilayer gas-sensitive resistive film including a resistive film formed of an aggregate of ultrafine particles of tin oxide and a resistive film formed of an aggregate of ultrafine metal particles of palladium will be described with reference to FIG. 9.

Referring to FIG. 9, an electrically insulating substrate 36 having a pair of comb-shaped electrodes 2 and 3 as shown in FIG. 1 is supported by a sample holder 38 within a vessel 37 with its electrode-bearing surface directed downward in FIG. 9. An evaporating material 40, which is one of Sn, SnO and $SnO_2$, is placed on an evaporator boat 39. Another evaporating material or palladium 42 is placed on another evaporator boat 41 disposed closely adjacent to the evaporator boat 39 within the vessel 37. Then, a vacuum pump (not shown) connected to an evacuation port 43 of the vessel 37 is driven to evacuate the internal space of the vessel 37 until a vacuum of the order of $10^{-6}$ Torr is established within the vessel 37. Subsequently, a valve at an oxygen gas admission port 44 is opened to admit oxygen gas into the vessel 37 so as to maintain an oxygen gas pressure of, for example, about 0.5 Torr. Electric power is then supplied from an evaporation power source 45 to the boat 39 to heat the boat 39, and the evaporating material 40 is allowed to evaporate for a period of time of from less than 20 seconds to several minutes in the oxygen gas atmosphere at about 0.5 Torr. When, for example, Sn is selected as the evaporating material 40, and the electric power of 120 watts to 160 watts is supplied to the boat 39, a gas-sensitive resistive film of ultrafine particles of tin oxide having a mean particle diameter of about 40 Å and having a thickness of about 20 μm, as shown in FIG. 1, is formed on the electrically insulating substrate 36. It is to be noted herein that a suitable mask is required so as to selectively deposit such a gas-sensitive resistive film of ultrafine particles of tin oxide to cover the electrodes on the electrical insulating substrate 36 in a pattern as shown in FIG. 1. The mean particle diameter specified above is calculated on the X-ray diffraction curve.

After the formation of the gas-sensitive resistive film of ultrafine particles of tin oxide, the vacuum pump (not shown) connected to the evacuation port 43 is driven again to evacuate the internal space of the vessel 37 until a vacuum of the order of $10^{-6}$ Torr is established again. Then, a valve at an inert gas admission port 46 is opened to admit an inert gas, for example, argon gas or helium gas into the vessel 37 to maintain, for example, an argon gas pressure of about 1.0 Torr. Subsequently, electric power is supplied from another evaporation power source 47 to the boat 41 to heat the boat 41, and the evaporating material 42 is allowed to evaporate for a period of time of from less than 20 seconds to several minutes in the argon gas atmosphere. When, for example, the electric power of 120 watts to 160 watts is supplied to the boat 41 for 1 minute, a film of ultrafine particles of palladium having a mean particle diameter of several ten Å and having a thickness of about 2 μm to 5 μm is deposited on the gas-sensitive resistive film formed of an aggregate of ultrafine particles of tin oxide having been deposited in the preceding step.

Although the resistance heating has been employed for the evaporation of the evaporating materials, by way of example, those skilled in the art will readily understand that induction heating, infrared heating or any other suitable heating may be employed in lieu of the resistance heating.

While the gas-sensitive resistive film of ultrafine particles of tin oxide exhibits a very high sensitivity to external factors such as gases including isobutane gas and water vapor, a multi-layer film comprising a gas-sensitive resistive film of ultrafine particles of tin oxide and an overlying film of ultrafine particles of palladium as described above exhibits a higher sensitivity to such gases.

In an experiment conducted by the inventors, a gas-sensitive resistive film of ultrafine particles of tin oxide 20 μm thick was formed in an oxygen gas atmosphere at 0.5 Torr, and then, a film of ultrafine particles of palladium 1.0 μm thick was deposited on the former film in an argon gas atmosphere at 1.0 Torr. The gas sensitivity of this multi-layer film was as high as about 1.9 times that of the single-layer film of ultrafine particles of tin ocide.

Figure 10:
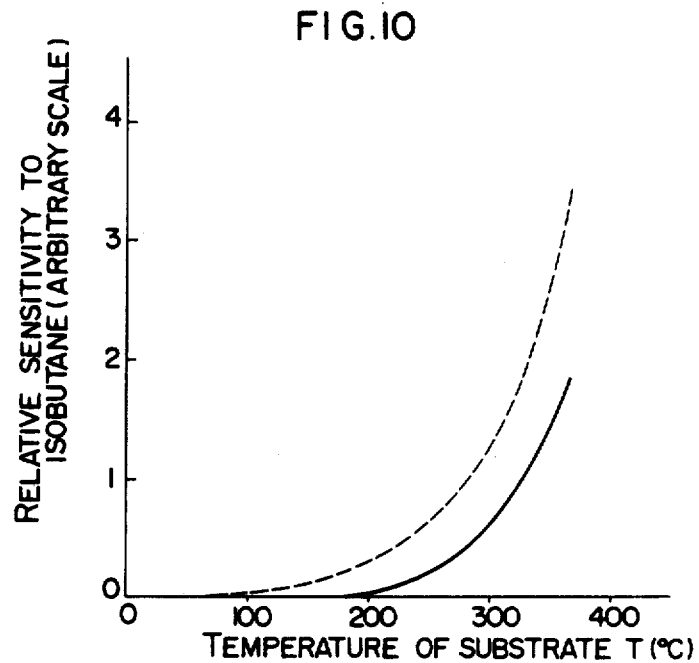
FIGS. 10 to 15 are graphs showing, by way of example, the electrical properties of the gas sensing element of the present invention manufactured by the method shown in FIG. 9.

FIG. 10 shows the dependence of the gas sensitivity of these films on the temperature of the electrically insulating substrate. It will be seen from FIG. 10 that the gas sensitivity of the gas-sensitive resistive film of multi-layer structure shown by the broken curve is higher in all the range of the temperature of the electrically insulating substrate than that of the gas-sensitive resistive film of single-layer structure shown by the solid curve. It will also be seen in FIG. 10 that the substrate temperature at which the gas sensitivity starts to appear is lower in the case of the gas-sensitive resistive film of multi-layer structure than in the case of the gas-sensitive resistive film of single-layer structure.

The gas-sensitive resistive film of multilayer structure comprising the single-layer film formed of an aggregate of ultrafine particles of tin oxide and the film of ultrafine particles of palladium manufactured according to the aforementioned method of the present invention showed good results when the single-layer film of ultrafine particles of palladium had a thickness of several μm, and the mean particle diameter of the ultrafine particles of palladium was about several ten Å or approximately equal to that of the ultrafine particles of tin oxide.

It will thus be appreciated that the gas-sensitive resistive film of multi-layer structure comprising the single-layer film of ultrafine particles of tin oxide and the overlying film of ultrafine particles of palladium manufactured by the method according to the present invention exhibits a greatly improved sensitivity to external factors acting thereupon such as gases including isobutane gas and water vapor, and the gas sensing device comprising this gas-sensitive resistive film of multilayer structure can operate at a lower operating temperature than that of single-layer structure. Thus, the gas sensing device exhibiting a higher sensitivity to gases can be easily provided.

A single-layer gas-sensitive resistive film comprising a mixture of ultrafine particles of tin oxide and palladium can be obtained by simultaneously supplying the electric power to the boats 39 and 41 from the respective power sources 45 and 47 in the apparatus shown in FIG. 9 thereby simultaneously evaporating the evaporating materials 40 and 42.

The characteristics of a gas sensing element comprising a single-layer gas-sensitive resistive film of ultrafine particles of tin oxide formed by a method similar to that described with reference to FIG. 9 will be described in detail presently.

The gas sensing characteristic of the gas sensing element comprising such a single-layer gas-sensitive resistive film of ultrafine particles of tin oxide varies considerably depending on the manufacturing conditions. While various manufacturing parameters affect the gas sensing characteristic of the gas sensing element, the gas sensing characteristic is most dependent upon the atmosphere in which the gas-sensitive resistive film of ultrafine particles of tin oxide is formed, especially, the pressure of oxygen gas in the atmosphere. The mean particle diameter of the ultrafine particles of tin oxide, formed at the constant temperature of an evaporator boat, is between 100 Å and 200 Å at an oxygen gas pressure of 10 Torr and several ten Å at an oxygen gas pressure of 1 Torr. Generally, the specific surface area of the ultrafine particles and the proportion of the surface energy to the total energy of the ultrafine particles vary greatly depending on the mean particle diameter of the ultrafine particles. The proportion of the number of surface atoms to the total number of atoms of the ultrafine particles of tin oxide formed at the oxygen gas pressure of 10 Torr is about 10%, and that of the ultrafine particles of tin oxide formed at the oxygen gas pressure of 1 Torr is about 45%. Thus, the surface energy, hence, the surface activity of the ultrafine particles of tin oxide reacting with gases including isobutane gas and water vapor varies depending on the pressure of oxygen gas supplied for the formation of the gas-sensitive resistive film of ultrafine particles of tin oxide. Also, the structure of the film of ultrafine particles of tin oxide deposited on the electrically insulating substrate varies depending on the pressure of oxygen gas. When the pressure of oxygen gas is 0.1 Torr, the film formed of an aggregate of ultrafine particles of tin oxide grows in a columnar structure perpendicular to the surface of the substrate, and the surface of the film is relatively flat and smooth although it includes local cracks. It is considered that, in this case, the ultrafine particles of tin oxide forming the film have a small mean particle diameter and are closely packed.

When the pressure of oxygen gas is 0.5 Torr, derangement tends to appear in the orientation of the film of ultrafine particles of tin oxide although the columnar structure remains still therein. This proves the fact that the mean particle diameter of the ultrafine particles of tin oxide is now considerably large or of the order of 30 Å, and that the binding force acting between the ultrafine particles of tin oxide is lower than in the case of the oxygen gas pressure of 0.1 Torr.

When the pressure of oxygen gas is 10 Torr, the unidirectional growth of the film formed of an aggregate of ultrafine particles of tin oxide disappears, and also, the film of ultrafine particles of tin oxide is no more columnar in its sectional structure. The film of ultrafine particles of tin oxide has now a spongy sectional structure, and its surface structure is also spongy like the sectional structure.

Figure 11:
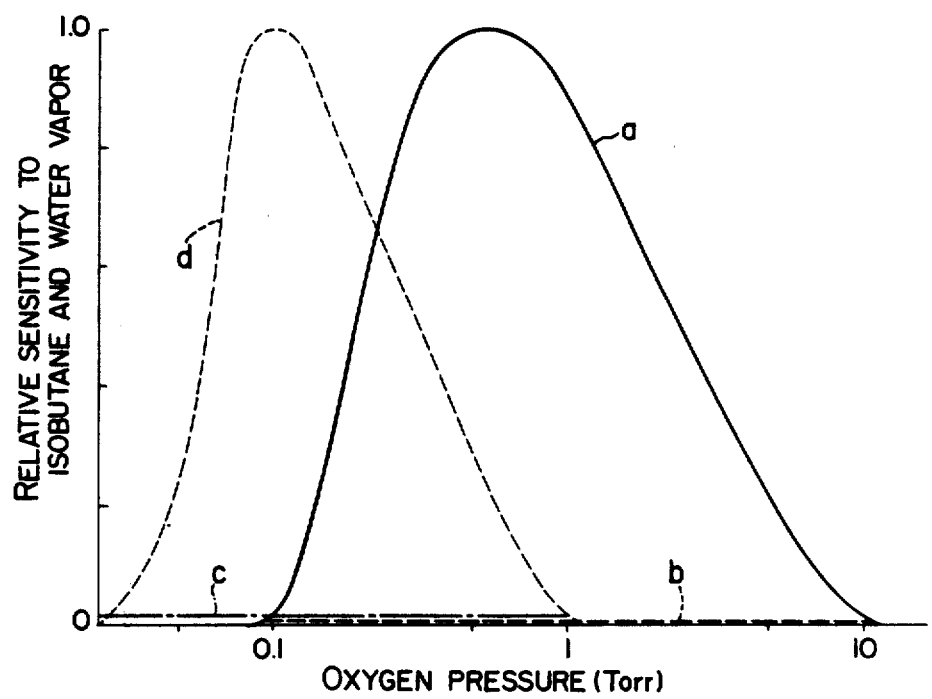

FIG. 11 shows how the sensitivity of the gas-sensitive resistive film of ultrafine particles of tin oxide to isobutane gas and water vapor is dependent upon the pressure of oxygen gas supplied during the deposition thereof.

As described above, the mean particle diameter, the manner of growth and the orientation of the gas-sensitive resistive film formed of an aggregate of ultrafine particles of tin oxide formed in the oxygen gas atmosphere vary depending on the pressure of oxygen gas supplied in the step of deposition. It is apparent therefore that the mode of reaction of the gas-sensitive resistive film of ultrafine particles of tin oxide with gases such as isobutane gas and water vapor varies depending on the pressure of oxygen gas supplied during the deposition of this film.

The solid curve a shown in FIG. 11 represents the result of measurement of the sensitivity of the gas sensing element comprising the gas-sensitive resistive film of ultrafine particles of tin oxide to isobutane gas when the temperature of the electrically insulating substrate was 300° C. It will be seen from this curve a that the gas sensing element comprising the gas-sensitive resistive film of ultrafine particles of tin oxide is sensitive to the isobutane gas when the film is formed in the oxygen gas atmosphere at the pressure between 0.1 Torr and 10 Torr.

The broken curve b in FIG. 11 represents the result of measurement of the sensitivity of the gas sensing element comprising the gas-sensitive resistive film of ultrafine particles of tin oxide to the isobutane gas when the electrically insulating substrate was not heated or its temperature was equal to the room temperature of 25° C. It will be seen from this curve b that the gas sensing element is not sensitive to the isobutane gas without regard to the pressure of oxygen gas supplied during the manufacture thereof.

The one-dot chain urve c in FIG. 11 represents the result of measurement of the sensitivity of the gas sensing element comprising the gas-sensitive resistive film formed of an aggregate of ultrafine particles of tin oxide to water vapor when the electrically insulating substrate was heated up to 300° C. It will be seen from this curve c that the gas sensing element is not sensitive to the water vapor at such a high temperature without regard to the pressure of oxygen gas supplied during the manufacture thereof.

The dotted curve d in FIG. 11 represents the result of measurement of the sensitivity of the gas sensing element comprising the gas-sensitive resistive film of ultrafine particles of tin oxide to the water vapor when the electrically insulating substrate was not heated, that is, its temperature is equal to the room temperature of 25° C. It will be seen from this curve d that the gas sensing element comprising the gas-sensitive resistive film of ultrafine particles of tin oxide is sensitive to the water vapor when the film is formed in the oxygen gas atmosphere at the pressure between 0.02 Torr and 1 Torr.

It will be apparent from FIG. 11 that the gas sensing element comprising the gas-sensitive resistive film of ultrafine particles of tin oxide formed in the oxygen gas atmosphere at the pressure between 0.1 Torr and 1 Torr can selectively sense the isobutane gas and water vapor at the temperatures of 300° C. and 25° C. or room temperature respectively when the measurement is carried out at such temperatures.

It will be understood from the above description that the gas sensing element comprising the gas-sensitive resistive film formed of an aggregate of ultrafine particles of tin oxide made by the method described can selectively measure the concentrations of gases, for example, isobutane gas and water vapor present in the same atmosphere by merely varying the temperature of the electrically insulating substrate of the single gas sensing element. As will be apparent from the above description, the fact that the single gas sensing element can measure such two different gases provides the advantage that the peripheral circuits can be made far simpler than when two gas sensing elements are used for that purpose.

Another embodiment of the manufacturing method will now be described. According to this embodiment of the manufacturing method, a gas sensing element is manufactured in which, without impairing the sensitivity to gases, the resistance value thereof is only lowered compared with the gas sensing element comprising the gas-sensitive resistive film of ultrafine particles of tin oxide manufactured by the aforementioned embodiment of the manufacturing method. In the presently described embodiment of the manufacturing method, a two-layer film is formed by varying the pressure of oxygen gas supplied into a vessel which is the same as that shown in FIG. 9. For example, a first film of ultrafine particles of tin oxide about 20 $\mu$m thick is formed in an oxygen gas atmosphere at a pressure of 0.5 Torr, and then, a second film of ultrafine particles of tin oxide about 5 $\mu$m thick is deposited on the first film. Three kinds of such a second film were deposited at different oxygen gas pressures of 0.1 Torr, 0.05 Torr and 0.003 Torr respectively to provide three kinds of gas sensing elements comprising multi-layer films formed of an aggregate of ultrafine particles of tin oxide having different mean particle diameters respectively. The isobutane gas sensitivity and resistance value of these three gas sensing elements were compared with those of a reference gas sensing element comprising a single-layer film of ultrafine particles of tin oxide formed in an oxygen gas atmosphere at a pressure of 0.5 Torr. The results proved that the resistance values of the gas sensing elements comprising the multi-layer films including the second films formed at the oxygen gas pressures of 0.1 Torr, 0.05 Torr and 0.003 Torr were about $\frac{1}{2}$, 1/10 and 1/40 respectively of the resistance value of the reference gas sensing element comprising the single-layer film formed at the oxygen gas pressure of 0.5 Torr, although all of them had the same gas sensitivity. The thickness of the upper layer in the two-layer film may have a limit. However, the gas sensitivity of these gas sensing elements was independent of the thickness of the upper layer when the thickness was smaller than at least 10 $\mu$m. Thus, the presently described embodiment of the manufacturing method according to the present invention is useful for the production of a gas sensing element for which a low resistance value is required from the structural aspect of the circuit in the gas sensing device.

Another embodiment of the manufacturing method will now be described. A step of heat treatment is added in order to further improve the gas sensitivity and to further reduce the resistance value of the gas sensing element comprising the gas-sensitive resistive film of ultrafine particles of tin oxide manufactured by the first-mentioned embodiment of the manufacturing method.

A gas-sensitive resistive film formed of an aggregate of ultrafine particles of tin oxide about 20 $\mu$m thick was formed in an oxygen gas atmosphere at a pressure of 0.5 Torr and was then subjected to heat treatment at 500° C. for 10 minutes in air according to the principle of the present embodiment of the manufacturing method. A comparison test was conducted to compare the above film with a similar gas-sensitive resistive film of ultrafine particles of tin oxide which was not subjected to such heat treatment.

In the test, these samples were heated up to and maintained at a temperature of 250° C. in an ambient atmosphere which had a temperature of 25° C. and a relative humidity of 60%, and their sensitivity to gaseous ethyl alcohol having a concentration of 100 ppm was measured. The gas sensitivity was represented by the ratio $R_o/R_G$ where $R_o$ is the resistance value in air, and $R_G$ is the resistance value in the gaseous ethyl alcohol having the concentration of 100 ppm. The gas sensitivity and the resistance value of the sample made according to the aforementioned method relative to those of the comparative sample are shown in Table 1. In this Table 1, both the gas sensitivity and the resistance value of the comparative sample are taken as 1.0.

TABLE 1

| Sample | Gas sensitivity | Resistance value |
| --- | --- | --- |
| Present embodiment | 9.5 | 1/5.2 |
| Comparative | 1.0 | 1.0 |

The above table clarifies the fact that both the gas sensitivity and the resistance value of the sample made according to the aforementioned embodiment are greatly improved compared with those of the comparative sample.

It is presumed that one of the factors realizing such a great improvement in both the gas sensitivity and the resistance value is attributable to the fact that the heat treatment in the oxygen containing atmosphere results in sufficient oxidization of the ultrafine particles of tin oxide forming the gas-sensitive resistive film thereby increasing the proportion of $SnO_2$ in the gas-sensitive resistive film formed of an aggregate of ultrafine particles of tin oxide.

This is also seen from the fact that the color of the gas-sensitive resistive film of ultrafine particles of tin oxide changes from yellowish white to white as a result of the heat treatment and also from the results of measurement by X-ray diffraction. It is to be pointed out, however, that the critical temperature of this heat treatment is the sintering temperature for the gas-sensitive resistive film of ultrafine particles of tin oxide. The heat treatment is desirably continued until the ultrafine particles of tin oxide are sufficiently oxidized. In the case of the presently described embodiment, good results were obtained by continuing the heat treatment at a temperature of 350° C. to 550° C. for 10 minutes to 30 minutes.

Needless to mention, the temperature and duration of heat treatment vary depending on the manufacturing conditions of the ultrafine particles of tin oxide, especially, the pressure of oxygen gas supplied during the deposition of the gas-sensitive resistive film of such ultrafine particles. The manufacturing conditions are preferably so selected that the temperature of heat treatment is higher than at least the operating temperature of the gas sensing element, and the temperature and duration of heat treatment are preferably so selected that the resistance value R of the gas sensing element starting to vary immediately after being heated is stabilized at the operating temperature of the element.

Another embodiment of the manufacturing method relates to the manufacture of a gas sensing element comprising a gas-sensitive resistive film of ultrafine particles of copper oxide.

A gas-sensitive resistive film of ultrafine particle of copper oxide formed by the aforementioned manufacturing method has such a characteristic that it can selectively sense the concentration of gases, that is, it can sense the concentration of water vapor when operating at the room temperature of 25° C., the concentration of gaseous ethyl alcohol when operating at a temperature of about 300° C., and the concentration of isobutane gas when operating at a temperature of about 500° C.

The aforementioned gas sensing element comprising the gas-sensitive resistive film of ultrafine particles of tin oxide can measure both the concentration of water vapor and the concentration of isobutane gas respectively at different operating temperatures. In a high temperature range, however, this gas sensing element comprising the gas-sensitive resistive film of ultrafine particles of tin oxide has not yet been successful in selectively sensing the concentration of gaseous ethyl alcohol and that of isobutane gas.

Figure 12:
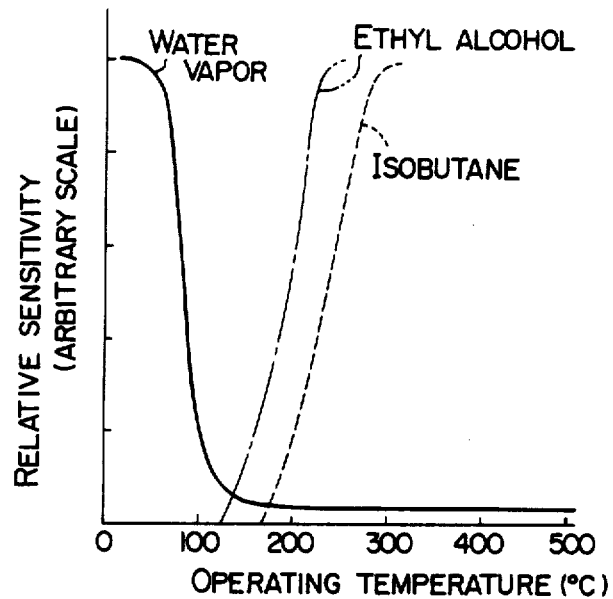

The gas sensitivity and the operating temperature of the gas sensing element comprising the gas-sensitive resistive film formed of an aggregate of ultrafine particles of tin oxide have an approximate relation therebetween as shown in FIG. 12. It will be seen from FIG. 12 that this gas sensing element can selectively sense the concentration of water vapor at an operating temperature equal to about the room temperature of 25° C. and the concentration of gaseous ethyl alcohol at an operating temperature of 150° C. to 200° C. Due to, however, the fact that the operating temperature range in which the gas sensing element is sensitive to isobutane gas is necessarily included within the operating temperature range in which it is sensitive to gaseous ethyl alcohol, this gas sensing element has been unable to selectively sense the concentration of isobutane gas.

Figure 13:
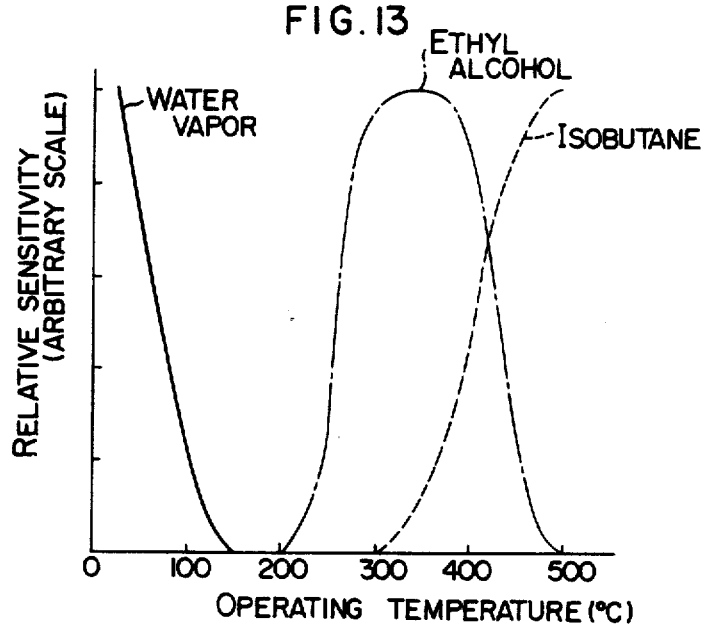

The gas sensitivity and the operating temperature of the gas sensing element comprising the gas-sensitive resistive film of ultrafine particles of copper oxide have an approximate relation therebetween as shown in FIG. 13. It will be clear from FIG. 13 that the gas sensitive element comprising the gas-sensitive resistive film of ultrafine particle of copper oxide formed by the previously described method according to the present invention is sensitive to water vapor only at an operating temperature equal to about the room temperature of 25° C., sensitive to gaseous ethyl alcohol only at an operating temperature of 250° C. to 300° C., and sensitive to isobutane gas only at an operating temperature of about 500° C. Thus, this gas sensing element can completely selectively sense the individual concentrations of water vapor, gaseous ethyl alcohol and isobutane gas.

This gas sensing element comprising the gas-sensitive resistive film formed of an aggregate of ultrafine particles of copper oxide can be formed by evaporating one of Cu, CuO and $Cu_2O$ in an oxygen gas atmosphere within a vessel which is the same as that shown in FIG. 9. When, for example, Cu selected as the evaporating material is placed on the boat in the oxygen gas atmosphere, and electric power of 70A to 80A at 3 volts is supplied for 1 minute to evaporate the evaporating material, a gas-sensitive resistive film of ultrafine particles of copper oxide about 10 μm thick is formed on the electrically insulating substrate.

The characteristic of the gas sensing element comprising the gas-sensitive resistive film of ultrafine particles of copper oxide varies considerably depending on the manufacturing conditions.

Among various parameters affecting the characteristic of this gas sensing element, the atmosphere in which the gas-sensitive resistive film of ultrafine particles of copper oxide is formed, that is, the pressure of oxygen gas in the atmosphere, is the most predominant parameter affecting the characteristic of the element.

When, for example, the gas-sensitive resistive film of ultrafine particles of copper oxide is formed in an oxygen gas atmosphere at a pressure higher than 1.0 Torr, CuO, which is an n-type semiconductor and stable in itself, is the principal component of the film. When, however, the film is formed in an oxygen gas atmosphere at a pressure lower than 1.0 Torr, the principal component of the film is $Cu_2O$ which a p-type semiconductor which is very active and is not stable in itself. In this case, the composition of the film tends to change even in an atmosphere at the room temperature of 25° C., and the electrical resistance value of the film varies incessantly. It is therefore necessary to apply suitable heat treatment to the film of ultrafine particles of $Cu_2O$ so as to turn this $Cu_2O$ into CuO which is stable in itself.

Gas sensing elements each comprising a gas-sensitive resistive film formed of an aggregate of ultrafine particles of copper oxide were formed at different pressures of oxygen gas and were then subjected to heat treatment in air at 500° C.

In the case of the gas sensing elements each comprising the gas-sensitive resistive film of ultrafine particles of copper oxide formed in an oxygen gas pressure at a pressure lower than 0.1 Torr, sintering of the ultrafine particles occurred during the step of heat treatment, and these gas sensing elements exhibited a very bad reproducibility of the resistance value relative to temperature variations.

When these gas sensing elements were formed in oxygen gas atmospheres at pressures of 0.25 Torr and 0.5 Torr, the principal component of the film immediately after the formation thereof was $Cu_2O$, and the resistance value of each of the these gas sensing elements was low or about 10 kΩ. However, the resistance value of the gas sensing elements could be increased by the step of heat treatment until finally it was saturated in about 60 minutes to 120 minutes. The saturated resistance value of the heat-treated gas sensing elements was about several ten times as large as the resistance value of the gas sensing elements before being subjected to the heat treatment, and the principal component of the film of ultrafine particles turned into CuO from $Cu_2O$. On the other hand, in the case of the gas sensing elements formed in oxygen gas atmospheres at pressures of 1.0 Torr and 2.5 Torr, the principal component of the film in each of these elements was CuO when analysed immediately after the formation thereof, and the gas sensing elements exhibited a considerably high resistance value or about several hunded kΩ. The resistance value of these gas sensing elements did not vary appreciably in spite of the heat treatment, and the principal component of the film continued to be CuO, which is stable in itself.

A test was conducted to find the gas sensitivity of the gas sensing element comprising the gas-sensitive resistive film formed of an aggregate of ultrafine particles of copper oxide formed in the oxygen gas atmosphere at the pressure of 0.25 Torr. In this test, the resistance value $R_o$ of the element in air at the room temperature of 25° C. and a relative humidity of 30% was taken as a reference or 1.0, and the ratio between this reference resistance value $R_o$ and the resistance value $R_x$ in each of water vapor (a relative humidity of 60%)/air, 0.2% gaseous ethyl alcohol/air and 0.2% isobutane gas/air was calculated. The results are shown in Table 2.

TABLE 2

| Atmosphere Temperature | 60% water vapor | 0.2% ethyl alcohol | 0.2% isobutane gas |
|---|---|---|---|
| 25° C. | 0.40 | 1.00 | 1.00 |
| 300° C. | 1.00 | 0.54 | 1.00 |
| 500° C. | 1.00 | 1.00 | 0.30 |

The numerical values shown in Table 2 were calculated on the basis of the resistance value of the gas sensing element measured after applying the heat treatment at 500° C. for a suitable duration thereby turning the copper oxide into stable CuO.

Figure 14:
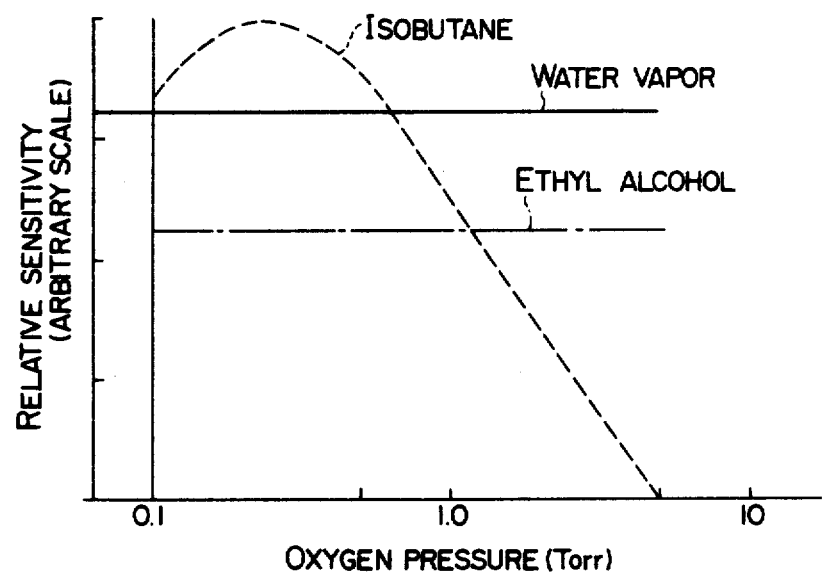

FIG. 14 shows the relation between the pressure of oxygen gas supplied during the formation of various gas sensing elements each comprising the gas-sensitive resistive film of ultrafine particles of copper oxide and the gas sensitivity of the elements to water vapor, gaseous ethyl alcohol and isobutane gas. It will be seen from FIG. 14 that the gas sensitivity of the gas sensing elements formed in oxygen gas atmospheres at pressures of 0.1 Torr to 5 Torr, does not exhibit any substantial dependence on the oxygen gas pressure when these gas sensing elements are used to sense the concentrations of water vapor and gaseous ethyl alcohol. However, the gas sensing element formed in the oxygen gas atmosphere at the pressure of 0.25 Torr exhibits its highest sensitivity to isobutane gas, and the sensitivity to isobutane gas is lowered with the increase in the oxygen gas pressure from 0.25 Torr. The gas sensing element formed in the oxygen gas atmosphere at the pressure of 5 Torr does not exhibit any sensitivity to isobutane gas. The reasons therefor have not yet been clarified to date.

It will be understood from the above description that the gas sensing element comprising the gas-sensitive resistive film formed of an aggregate of ultrafine particles of copper oxide is remarkably useful for the purpose of gas concentration measurement, since the single gas sensing element can simultaneously and selectively sense the concentrations of different gases, for example, water vapor, gaseous ethyl alcohol and isobutane gas present in a single atmosphere by merely operating it at different temperatures.

An isobutane gas sensing device comprising a gas sensing element comprising such a gas-sensitive resistive film of ultrafine particles of copper oxide finds thus a useful practical application in measurement of various gas concentrations, since the presence of ethyl alcohol and water vapor does not in any way obstruct the isobutane gas sensing operation.

Figure 15:
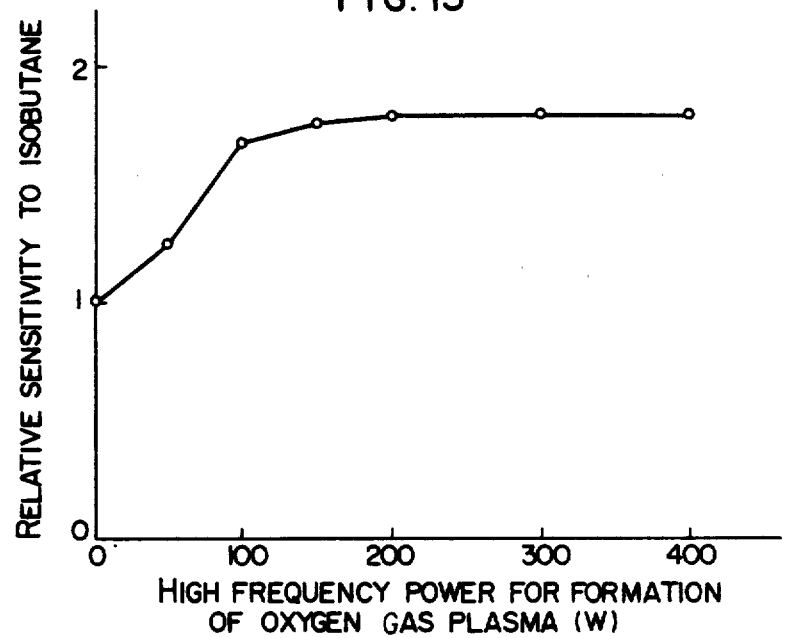

A gas sensing element comprising a gas-sensitive resistive film of ultrafine particles of tin oxide can highly sharply sense gases such as isobutane gas and water vapor as described already. The gas sensitivity of such a gas sensing element can be further improved by a novel manufacturing method according to the present invention which will be described presently. This manufacturing method is featured by the fact that the gas-sensitive resistive film of ultrafine particles of tin oxide deposited to cover the electrodes on the electrical insulating substrate according to the first-mentioned embodiment of the manufacturing method, is exposed to an atmosphere of plasma of oxygen gas. For example, the gas-sensitive resistive film of ultrafine particles of tin oxide is placed for about 30 minutes in an atmosphere of plasma of oxygen gas supplied at a flow rate of 1 l/minute. FIG. 15 shows the sensitivity to isobutane gas of the gas sensing element subjected to activation treatment in the plasma of oxygen gas. It will be seen in FIG. 15 that the gas sensitivity increases with the increase in the high-frequency power supplied for the formation of the plasma of oxygen gas and saturates substantially when the supplied power exceeds a level of, for example, 100 watts. The gas sensitivity of the gas sensing element comprising the gas-sensitive resistive film of ultrafine particles of tin oxide thus activated is about 1.8 times as high as that of the element before being subjected to the activation treatment by the plasma of oxygen gas.

It will thus be appreciated that, in the last-mentioned manufacturing method described, a gas sensing element comprising a gas-sensitive resistive film of ultrafine particles of tin oxide is exposed to an atmosphere of plasma of oxygen gas to be greatly improved its gas sensitivity, so that a gas sensing device capable of sensing gases with a higher sensitivity can be manufactured.

What we claim is:

1. A method of manufacturing a gas sensing device comprising the step of evaporating a material including at least one of a metal and its oxide in an atmosphere containing oxygen gas at a reduced pressure of an atmosphere containing an inert gas at a reduced pressure, thereby depositing a gas-sensitive resistive film of ultrafine particles having a mean diameter of between 10 and several hundred angstroms of said material on one of the major surfaces of a substrate of an electrical insulating material formed with electrodes to provide a gas sensing element.

2. A method of manufacturing a gas sensing device as claimed in claim 1, wherein, in said step of evaporation, a plurality of kinds of materials including at least one of said metal and its oxide are evaporated in an atmosphere containing oxygen gas at a reduced pressure thereby forming a gas-sensitive resistive film of ultrafine particles of oxides of said materials.

3. A method of manufacturing a gas sensing device as claimed in claim 1, wherein, in said step of evaporation, said material including at least one of said metal and its oxide is evaporated a plurality of times in an atmosphere containing oxygen gas at a reduced pressure or an atmosphere containing an inert gas at a reduced pressure, thereby forming a laminated gas-sensitive resistive film of ultrafine particles of said material.

4. A method of manufacturing a gas sensing device as claimed in claim 1, wherein said gas sensing element comprising said gas-sensitive resistive film of ultrafine particles of said material is then subjected to heat treatment in an atmosphere of oxygen gas or an atmosphere containing oxygen gas.

5. A method of manufacturing a gas sensing device as claimed in claim 4, wherein the temperature of the heat treatment of said gas sensing element comprising said gas-sensitive resistive film of ultrafine particles of said material is selected to be higher than at least the operating temperature of said gas sensing element.

6. A method of manufacturing a gas sensing device as claimed in claim 4, wherein the duration of the heat treatment on said gas sensing element comrpsing said gas-sensitive resistive film of ultrafine particles of said material in the atmosphere of oxygen gas or the atmosphere containing oxygen gas is selected to be longer at least the length of time required for the stabilization of the resistance value of said gas sensing element comprising said gas-sensitive resistive film of ultrafine particles.

7. A method of manufacturing a gas sensing device as claimed in claim 4, wherein said gas-sensitive resistive film of ultrafine particles is a gas-sensitive resistive film of ultrafine particles of copper oxide, and said gas sensing element comprising this gas-sensitive resistive film of ultrafine particles of copper oxide is subjected to the heat treatment in the atmosphere of oxygen gas or the atmosphere containing oxygen gas, so that said gas-sensitive resistive film of ultrafine particles of copper oxide thus heat-treated includes CuO as its principal component.

8. A method of manufacturing a gas sensing device as claimed in claim 4, wherein said gas-sensitive resistive film of ultrafine particles is a gas-sensitive resistive film of tin oxide, and said gas sensing element comprising this gas-sensitive resistive film of tin oxide is subjected to the heat treatment in the atmosphere of oxygen gas or the atmosphere containing oxygen gas, so that said gas-sensitive resistive film of ultrafine particles of tin oxide thus heat-treated includes $SnO_2$ as its principal component.

9. A method of manufacturing a gas sensing device as claimed in claim 1, wherein said gas sensing element comprising said gas-sensitive resistive film of ultrafine particles formed by the step of evaporation is then exposed to an atmosphere of plasma of oxygen gas.

* * * * *